United States Patent [19]

Sheng et al.

[11] 4,237,314

[45] Dec. 2, 1980

[54] PHENYL ACETIC ACID PREPARATION

[75] Inventors: Ming N. Sheng; Jar-Lin Kao, both of Cherry Hill, N.J.

[73] Assignee: Atlantic Richfield Company, Los Angeles, Calif.

[21] Appl. No.: 73,050

[22] Filed: Sep. 6, 1979

[51] Int. Cl.$^3$ .............................................. C07C 57/30
[52] U.S. Cl. .................................................. 562/496
[58] Field of Search ........................................ 562/496

[56] References Cited

U.S. PATENT DOCUMENTS

| | | | |
|---|---|---|---|
| 3,651,101 | 3/1972 | Boldt et al. | 260/410.5 |
| 3,654,486 | 2/1972 | Boldt et al. | 260/479 R |
| 4,048,238 | 9/1977 | Gardner et al. | 260/618 |

OTHER PUBLICATIONS

Bergman, et al., Tetrahedron Letters, vol. 35, pp. 3279–3282 (1978).

*Primary Examiner*—Alan Siegel
*Attorney, Agent, or Firm*—John R. Ewbank

[57] ABSTRACT

Phenyl acetic acid is prepared by the reaction of molecular oxygen and the combination of acetic acid and benzene in the presence of a catalytic system featuring both tellurium and halide, the unit atomic ratio of halide to tellurium being within a range from about 3 to about 20, at a temperature within a range from about 100° C. to about 200° C. at a pressure within a range from about 1 to about 15 atmospheres.

6 Claims, No Drawings

PHENYL ACETIC ACID PREPARATION

PRIOR ART

The esters of phenylacetic acid occur naturally, and are employed in artificial flavors and perfumes. Salts of phenylacetic acid are utilized in the fermentation of penicillin. In the United States the production and consumption of phenylacetic acid apparently exceeds several million pounds per year. Apparently, there are several domestic manufactures of phenylacetic acid. Some literature indicates that the hydrolysis of benzylnitrile is the only commercial method of manufacture. A variety of syntheses have been proposed in scholarly publications.

Although reactions with molecular oxygen have sometimes been appropriate for a dehydrogenation reaction or for the formation of organic compounds having some oxygen derivative at the point of reaction, there has been general consensus amongst organic chemists familiar with reaction mechanisms that one should not rely upon a reaction with molecular oxygen to bring about the formation of carbon-carbon bond. Because the market price of acetic acid and the market price of benzene have each consistently been a small fraction of the price at which phenylacetic acid has been sold, there has been a long standing demand for methods of preparing phenylacetic acid from these two relatively inexpensive starting materials. Some scholarly procedures for such a synthesis have involved many steps involving many purifications.

Heretofore, there have been literature descriptions relating to the use of catalyst systems comprising tellurium halide. Burkman et al, Tetrahedron Letters, Vol. 35, pgs. 3279-3282, (1978) describe the reaction of toluene with acetic acid in the presence of a combination of lithium bromide and tellurium dioxide to form benzyl acetate derivatives of toluene in the absence of pressurized oxygen. Such reaction involves the use of lithium bromide and tellurium dioxide dissolved in acetic acid at 120° C. Said article hypothesizes an intermediate in which the tellurium oxide oxidizes one of the hydrogens on the acetic acid to form an oxide carbine group, possibly free or possibly complexed with the tellurium, capable of adding to an aromatic hydrogen to provide the benzyl acetate group. As explained by Heiba et al, Journal American Chemical Society, Vol. 90, 2706 (1968), lead tetra acetate can lead to a similar formation of benzyl acetate derivatives of aromatic substrates. The chemical industry has generally ignored reactions involving the consumption of costly oxidizing agents of the type of tellurium dioxide and/or lead tetra acetate and greatly favored any reaction utilizing molecular oxygen as an oxidant and utilizing an appropriate catalyst.

FIELD OF INVENTION

This invention relates to the preparation of phenyl acetic acid. This invention concerns the utilization of catalyst systems of the tellurium halide type for promoting reactions involving molecular oxygen.

SUMMARY OF INVENTION

Molecular oxygen reacts with a mixture of benzene and acetic acid to form phenyl acetic acid in the presence of a catalyst system featuring the presence of both tellurium and a halide compound, the ratio of halide to tellurium being from about 3 to about 20 atoms of halide per atom of tellurium.

The nature of the invention is further clarified by a plurality of examples.

DESCRIPTION OF PREFERRED EMBODIMENT

EXAMPLE 1

A Fisher-Porter glass reactor was equipped with a teflon-coated magnetic stirring bar, a gas inlet, and the other appropriate components for a pressurized reaction. The reactor had a capacity of about 240 mililiters and was provided with 99.59 g of acetic acid and 12 g of benzene. The acetic acid served both as a reactant and solvent. The catalyst system, consisting of 8.41 g of tellurium tetrabromide was dissolved in the reaction mixture. The mixture, comprising acetic acid, benzene, and tellurium tetrabromide, was heated at 150° C. under 16 psig of oxygen for 6 hours. The conversion of the benzene was about 13.3%, permitting the recovery of 10.4 g of unreacted benzene. After removing the acetic acid by distillation, there was the recovery of 2.45 g of phenylacetic acid, corresponding to a selectivity of 88.1% of the benzene converted. Some of the tellurium tetrabromide apparently reacted with the acetic acid to form bromoacetic acid, which can be hypothecized as an intermediate in the reaction. From the reaction product there was recovered 3.72 g of bromoacetic acid, corresponding to about 31% of the bromine content of the tellurium tetrabromide.

Such formation of phenylacetic acid was a surprising and unexpected result from the catalytic oxidation reaction, inasmuch as several other products might have been expected as more plausible than phenylacetic acid. The high selectivity for phenylacetic acid stimulates greater interest in the reaction. It can be noted that tellurium content of the tellurium tetrabromide constitutes about 2.4 weight percent of the acetic acid. Similarly, the bromine (a member of the halogen group) content corresponds to 6% of the acetic acid.

EXAMPLES 2-16

Phenylacetic acid is prepared following the general procedure of Example 1, but with the modifications indicated by Table 1, leading to the preparation of phenyl acetic acid.

TABLE 1

| Example | gAcOH | $gC_6H_6$ | gTe | gX | Te Type | X Type | °C. | Hours | $O_2$psig | Overall Yield of $C_6H_5CH_2CO_2H$ |
|---|---|---|---|---|---|---|---|---|---|---|
| 2 | 100 | 10 | 2 | 8 | $TeCl_4$ | $NH_4Cl$ | 100 | 24 | 4 | fair |
| 3 | 100 | 5 | 1 | 10 | $TeBr_4$ | $NH_4Br$ | 140 | 16 | 30 | fair |
| 4 | 100 | 80 | 1 | 10 | $TeO_2$ | LiBr | 175 | 24 | 100 | good |
| 5 | 100 | 30 | 1 | 10 | $TeO_2$ | LiBr | 160 | 30 | 100 | good |
| 6 | 100 | 25 | 1 | 10 | $TeO_2$ | LiBr | 150 | 6 | 200 | good |
| 7 | 100 | 25 | 2 | 10 | $TeO_2$ | LiI | 120 | 4 | 10 | poor |
| 8 | 100 | 25 | 0.1 | 1 | $TeO_2$ | LiI | 150 | 12 | 50 | fair |
| 9 | 100 | 25 | 2 | 10 | $TeO_2$ | LiCl | 200 | 2 | 75 | fair |

TABLE 1-continued

| Example | gAcOH | gC6H6 | gTe | gX | Te Type | X Type | °C. | Hours | O2psig | Overall Yield of C6H5CH2CO2H |
|---|---|---|---|---|---|---|---|---|---|---|
| 10 | 100 | 25 | 1 | 10 | Te | K I | 160 | 20 | 75 | fair |
| 11 | 100 | 25 | 1 | 10 | TeCl4 | CaI2 | 145 | 18 | 15 | fair |
| 12 | 100 | 25 | 3 | 7 | TeBr2 | BrCH2CO2H | 170 | 72 | 45 | good |
| 13 | 100 | 25 | 2 | 9 | TeI4 | NaI | 160 | 48 | 20 | good |
| 14 | 100 | 25 | 1 | 8 | TeI2 | LiI | 130 | 12 | 80 | fair |
| 15 | 100 | 25 | 5 | 10 | TeCl2 | LiBr | 150 | 48 | 10 | fair |
| 16 | 100 | 25 | 1 | 4 | (CH3)2Te | LiBr | 160 | 24 | 90 | fair |

By a series of tests resembling Examples 1–16, it is established that the preparation of phenylacetic acid requires the use of acetic acid as both a reactant and a solvent, the concentration of the other components in the reaction mixture conveniently being expressed as a percentage of the amount of acetic acid in the reaction mixture. The preparation may be either batchwise or continuous. The benzene weight concentration should be within the range from about 5% to about 80% of the acetic acid, preferably about 10% to about 30%. The tellurium concenration should be within the range from about 0.1% to about 5% of the weight of acetic acid. The halide concentration (comprising any halide in the tellurium compound) should be within a range from about 1% to about 10% by weight, preferably about 3% to about 8%. The temperature must be within a range from about 100° C. to about 200° C., preferably 130°–175° C. The oxygen pressure should be within a range from about 4 psig, preferably about 10 to about 100 psig. There is always a storchiometric excess of oxygen and the oxygen pressure is always above that which corresponds to ambient atmospheric pressure. The atomic ratio of halide to tellurium must be within the range from 3 to 20 and preferably is from 4 to 10. The tellurium compound must be selected from the group consisting of oxides of tellurium, $TeCl_2$, $TeCl_4$, $TeBr_2$, $TeBr_4$, $TeI_2$, $TeI_4$, organic tellurium compounds, and mixtures thereof. The halide compound should be introduced into the reaction mixture as a salt of an alkali, ammonia, an alkaline earth, a tellurium compound, or a mixture thereof. A haloacetic acid such as bromoacetic acid can be introduced as a part of the halide, but only if measures for minimizing formation of aromatic acids having a plurality of acetic acid groups attached to the nucleus.

Such a haloacid may be an intermediate in the reaction mechanism for formation of phenylacetic acid.

Various modifications of the invention are possible without departing from the scope of the appended claims.

The invention claimed is:

1. The method preparing phenyl acetic acid which consists of preparing a reaction mixture consisting essentially of benzene, acetic acid, and a catalyst system of the tellurium halide type, said catalyst system consisting essentially of the combination of a tellurium compound and halogen compound, the unit atom ratio of halogen to tellurium being within a range from about 3 to about 20 and causing molecular oxygen to react with said reaction mixture within a range from 100° C. to 200° C., and at an oxygen pressure within a range from 4 psig to 200 psig for from 2 to 72 hours to prepare phenyl acetic acid.

2. The method of claim 1 in which the benzene weight concentration is within the range from about 5% to about 80% of the acetic acid.

3. The method of claim 1 in which the tellurium concentration is within the range from about 0.1% to about 5% of the weight of acetic acid.

4. The method of claim 1 in which the halide concentration is within a range from about 1% to about 10% of the weight of acetic acid.

5. The method of claim 1 in which tellurium tetrabromide is the catalyst system.

6. The method of preparing phenyl acetic acid which consists of subjecting molecular oxygen at an oxygen pressure above that which corresponds to ambient atmospheric pressure to a reaction mixture consisting essentially of acetic acid, benzene and tellurium tetrabromide at about 150° C. for about six hours.

* * * * *